(12) United States Patent
Miura

(10) Patent No.: US 10,092,216 B2
(45) Date of Patent: Oct. 9, 2018

(54) DEVICE, METHOD, AND NON-TRANSITORY COMPUTER-READABLE MEDIUM FOR IDENTIFYING BODY PART IMAGED BY ENDOSCOPE

(71) Applicant: FUJIFILM Corporation, Tokyo (JP)

(72) Inventor: Nobuyuki Miura, Tokyo (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 54 days.

(21) Appl. No.: 15/083,903

(22) Filed: Mar. 29, 2016

(65) Prior Publication Data

US 2016/0292498 A1    Oct. 6, 2016

(30) Foreign Application Priority Data

Mar. 30, 2015   (JP) ................................. 2015-070156

(51) Int. Cl.
*A61B 1/05*      (2006.01)
*G06K 9/62*      (2006.01)
(Continued)

(52) U.S. Cl.
CPC ............ *A61B 5/066* (2013.01); *A61B 1/0005* (2013.01); *A61B 1/00009* (2013.01); *A61B 1/00154* (2013.01); *A61B 1/01* (2013.01); *A61B 5/064* (2013.01); *G06T 7/0016* (2013.01); *G06T 7/74* (2017.01); *H04N 5/23293* (2013.01); *A61B 2034/2065* (2016.02);
(Continued)

(58) Field of Classification Search
CPC .. G06K 9/6201; G06K 9/6202; G06K 9/6215; G06K 2209/05; G06K 2209/051; G06T 7/0012; G06T 7/0014; G06T 7/0016; G06T 2207/10068; A61B 1/00009; A61B 1/04; A61B 1/05; A61B 2034/2065
See application file for complete search history.

(56) References Cited

U.S. PATENT DOCUMENTS

2010/0128116 A1*   5/2010   Sato et al. ...................... 348/65
2015/0208947 A1    7/2015   Tojo
(Continued)

FOREIGN PATENT DOCUMENTS

| JP | 4262741 B2 | 5/2009 |
| JP | 2011244937 A | 12/2011 |
| JP | 2012-165838 A | 9/2012 |
| JP | 2013094562 A | 5/2013 |
| JP | 2014-76174 A | 5/2014 |

OTHER PUBLICATIONS

Machine translation of JP 2013-94562 A, dated May 20, 2013.*
(Continued)

*Primary Examiner* — Andrew W Johns
(74) *Attorney, Agent, or Firm* — Sughrue Mion, PLLC

(57) ABSTRACT

In an endoscope system, an insertion amount of an insertion unit is detected based on camera images captured by two cameras provided to a mouthpiece. Then, past images of a predetermined range corresponding to the detected insertion amount are acquired from a past image storage unit. A current image is compared with each of the acquired past images to calculate similarity between the current image and each of the past images. A body part captured in the past image having the highest similarity with the current image is determined to be the body part captured in the current image.

10 Claims, 11 Drawing Sheets

(51) Int. Cl.
*A61B 5/06* (2006.01)
*G06T 7/00* (2017.01)
*A61B 1/00* (2006.01)
*A61B 1/01* (2006.01)
*H04N 5/232* (2006.01)
*G06T 7/73* (2017.01)
*H04N 5/225* (2006.01)
*A61B 34/20* (2016.01)

(52) U.S. Cl.
CPC .............. *G06T 2207/10068* (2013.01); *G06T 2207/30092* (2013.01); *H04N 2005/2255* (2013.01)

(56) References Cited

U.S. PATENT DOCUMENTS

2015/0208958 A1* 7/2015 Kaku ................... A61B 5/1459
600/339
2016/0353970 A1* 12/2016 Inoue ................. A61B 1/00006

OTHER PUBLICATIONS

Machine translation of JP 2011-244937 A, dated Dec. 8, 2011.*
Notification of Reasons for Refusal, dated Feb. 16, 2018, in corresponding JP Application No. 2015-070156, 7 pages in English and Japanese.

* cited by examiner

DEVICE, METHOD, AND NON-TRANSITORY COMPUTER-READABLE MEDIUM FOR IDENTIFYING BODY PART IMAGED BY ENDOSCOPE

CROSS-REFERENCE TO RELATED APPLICATIONS

The present application claims priority under 35 U.S.C. § 119 to Japanese Patent Application No. 2015-070156, filed Mar. 30, 2015. Each of the above applications is hereby expressly incorporated by reference, in its entirety, into the present application.

BACKGROUND OF THE INVENTION

1. Field of the Invention

The present invention relates to a device, a method, and a non-transitory computer-readable medium for identifying a body part imaged by an imaging unit provided at a distal end of an insertion section of an endoscope.

2. Description Related to the Prior Art

Endoscopes for capturing images of a patient's body cavity are widely known. An insertion section, which incorporates an imaging unit at its distal end, of the endoscope is inserted into the patient's body cavity and the image is captured by the imaging unit. The captured image is displayed on a monitor in real time. A doctor observes an imaged body part through the monitor.

As is well-known, the insertion section of the endoscope is provided with a distal portion, a flexible portion, and a flexible tube disposed in this order from the distal end. The distal portion incorporates the imaging unit. The flexible portion bends to change the direction of the distal portion. The flexible tube is flexible. An operation unit is connected to the proximal end of the insertion section. The operation unit is provided with an operation member (e.g. an angle knob), a shutter button, and the like. The operation member is used for bending the flexible portion. The shutter button allows the imaging unit to record a still image.

In an endoscopic examination, it is necessary for the doctor to perform the observation while knowing the imaged body part, for example, whether the imaged body part is esophagus or stomach, or whether the imaged body part is cardia, pylorus, or gastric angle of the stomach. However, it is difficult to distinguish the body part (e.g. a gastrointestinal tract) being subjected to the endoscopic examination, through visual observation of the image displayed on the monitor, so that the imaged body part may not be identified correctly. To solve this problem, an apparatus for identifying the body part being imaged has been developed.

For example, Japanese Patent No. 4262741 and US2015/0208947 (corresponding to Japanese Patent Laid-Open Publication No. 2014-076174) disclose an apparatus for identifying an imaged body part based on an insertion amount of the insertion section, a bend amount of the insertion section (the flexible portion), and a rotation amount of the insertion section about its axis. In an oral examination, in which the endoscope is inserted through the patient's mouth, such as an examination of an upper gastrointestinal tract, the insertion amount and the rotation amount are detected based on a displacement amount of the insertion section relative to, for example, a mouthpiece attached to the patient's mouth. The bend amount is detected based on, for example, an operation amount of the operation member for bending the flexible portion.

Japanese Patent Laid-Open Publication No. 2012-165838 discloses a technique to identify the imaged body part. According to this technique, three-dimensional image data of the patient's body cavity is generated based on an image acquired from a CT (Computed Tomography) examination or an MRI (Magnetic Resonance Imaging) examination, the insertion amount of the insertion section, the bend amount, and the rotation amount of the insertion section. The three-dimensional image data is compared with an image (current image) being captured, to identify the imaged body part.

However, the method for identifying the imaged body part based on the insertion amount, the bend amount, and the rotation amount as described in the Japanese patent No. 4262741 and the US2015/0208947 has low accuracy in identifying the imaged body part. Even if the insertion amount is the same, the imaged body part may vary from patient to patient, according to the individual difference (body shape, age, gender, or the like). The imaged body part identified based on the insertion amount may be different from the body part actually being imaged.

The rotation amount is detected based on the displacement amount of the insertion section relative to the mouthpiece attached to the patient's mouth. In other words, the rotation amount is detected relative to the direction of the patient's mouth. In case where the direction of the patient's mouth changes (e.g. in case where the patient changes the direction of his face) during the examination, rotation of the insertion section may be detected by error even if the insertion section itself has not been rotated. The bend amount is detected based on the operation amount of the operation member. A bend direction of the flexible portion varies according to a change in the rotation amount, which is the reference for determining the bend direction. For example, a shift of up to 90 degrees may occur between the actual imaging direction and the imaging direction determined based on the detected bend amount and the detected rotation amount.

According to the method described in the Japanese Patent Laid-Open Publication No. 2012-165838, the three-dimensional image data of the patent's body cavity is generated and the imaged body part is identified based on the result of the comparison between the three-dimensional image data and the current image. This method has higher accuracy in identifying the imaged body part than the method described in the Japanese Patent No. 4262741 and US2015/0208947. However, the method described in the Japanese Patent Laid-Open Publication No. 2012-165838 needs time and effort to generate the three-dimensional image data of the patient's body cavity based on the examination data obtained from the CT examination or the MRI examination performed in addition to the endoscopic examination.

SUMMARY OF THE INVENTION

An object of the present invention is to provide a device, a method, and a non-transitory computer-readable medium for identifying a body part imaged by an endoscope, capable of easily improving accuracy in identifying the imaged body part.

In order to achieve the above and other objects, a body part identification device according to an aspect of the present invention comprises an insertion amount detector, a current image acquisition unit, a past image acquisition unit, and a body part identifier. The insertion amount detector detects an insertion amount of the insertion section inserted into the body cavity. The current image acquisition unit acquires the current image. The past image acquisition unit acquires at least one past image from a past image storage unit based on the insertion amount detected by the insertion amount detector. The past image storage unit stores the past images captured in at least one past endoscopic examination. The body part identifier identifies the imaged body part in the current image through comparing the past image acquired by the past image acquisition unit with the current image and determining the past image similar to the current image. The body part identification device is used for an endoscope. The endoscope inserts an insertion section into a body cavity of a patient and captures an image of the body cavity. The distal portion of the insertion section incorporates an imaging unit. The body part identification device identifies the imaged body part in the current image currently being captured by the imaging unit.

It is preferred that the body part identifier determines the past image having the highest similarity with the current image among the past images used for the comparison with the current image, and determines a body part in the determined past image to be the imaged body part in the current image.

It is preferred that the body part identification device further comprises a correspondence table representing correspondence between the insertion amount and a candidate for the imaged body part. It is preferred that the past image acquisition unit refers to the correspondence table and determines the candidate for the imaged body part based on the insertion amount detected by the insertion amount detector, and acquires the past image corresponding to the determined candidate from the past image storage unit.

It is preferred that the body part identification device further comprises a bend amount detector and a rotation amount detector. The bend amount detector detects a bend amount of the insertion section. The rotation amount detector detects a rotation amount of the insertion section about an axis of the insertion section. It is preferred that the past image acquisition unit acquires the past image based on the insertion amount, the bend amount, and the rotation amount.

It is preferred that the past image acquisition unit acquires the past image of a patient of interest from the past image storage unit. The patient of interest is imaged in the current image.

It is preferred that the past image acquisition unit acquires the past image of another patient from the past image storage unit. The another patient is different from a patient of interest imaged in the current image.

It is preferred that the past image acquisition unit acquires the past image of a patient of interest in a case where the past image storage unit contains the past image of the patient of interest and the past image acquisition unit acquires the past image of another patient different from the patient of interest in a case where the past image storage unit does not contain the past image of the patient of interest. The patient of interest is imaged in the current image.

It is preferred that the body part identification device further comprises a screen generator and a display controller. The screen generator generates an endoscopic examination support screen. The endoscopic examination support screen displays the current image and the imaged body part in the current image. The imaged body part is identified by the body part identifier. The display controller controls a display of the endoscopic examination support screen.

It is preferred that the endoscopic examination support screen displays the current image and the past image in a comparable manner. The past image contains the same imaged body part as in the current image. The imaged body part in the current image is identified by the body part identifier.

An aspect of the present invention provides a body part identification method allowing a body part identification device to perform a detection step, a current image acquisition step, a past image acquisition step, and an identification step. In the detection step, an insertion amount of the insertion section inserted into the body cavity is detected. In the current image acquisition step, a current image is acquired. In the past image acquisition step, at least one past image is acquired from a past image storage unit based on the insertion amount. The past image storage unit stores the past images captured in at least one past endoscopic examination. In the identification step, the imaged body part in the current image is identified through comparing the acquired past image with the current image and determining the past image similar to the current image. The body part identification method is used for an endoscope. The endoscope inserts an insertion section into a body cavity of a patient and captures an image of the body cavity. A distal portion of the insertion section incorporates an imaging unit. The body part identification method identifies an imaged body part in a current image currently being captured by the imaging unit.

An aspect of the present invention provides a non-transitory computer-readable medium having instructions stored therein which, when executed by a computer, cause the computer to perform operations for identifying an imaged body part in a current image currently being captured by an imaging unit. The imaging unit is incorporated in a distal portion of an insertion section of an endoscope. The endoscope inserts the insertion section into a body cavity of a patient and captures an image of the body cavity. The operations include a detection operation, a current image acquisition operation, a past image acquisition operation, and an identification operation. In the detection operation, an insertion amount of the insertion section inserted into the body cavity is detected. In the current image acquisition operation, a current image is acquired. In the past image acquisition operation, at least one past image is acquired from a past image storage unit based on the insertion amount. The past image storage unit stores the past images captured in at least one past endoscopic examination. In the identification operation, the imaged body part in the current image is identified through comparing the acquired past image with the current image and determining the past image similar to the current image.

According to the aspects of the present invention, the accuracy in identifying an imaged body part is improved easily.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS

First Embodiment

Figure 1:
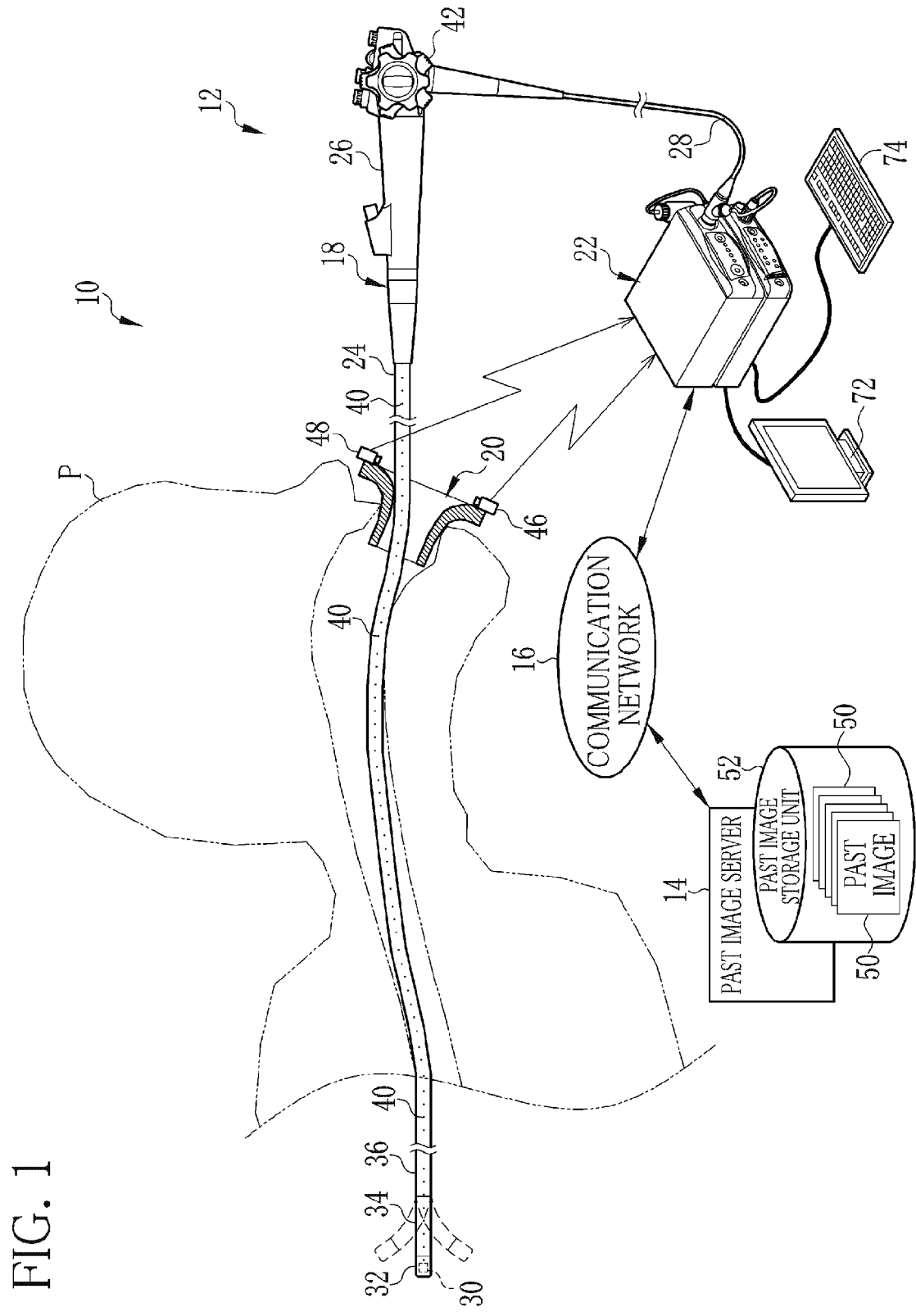
FIG. 1 is an explanatory view illustrating an endoscope system.

As illustrated in FIG. 1, an endoscope system 10 comprises an endoscope apparatus 12 and a past image server 14, which are interconnected through a communication network 16 such as the Internet or a LAN (Local Area Network). The endoscope apparatus 12 comprises an endoscope 18, a mouthpiece 20, a processor device 22, a display 72, and a keyboard 74. The processor device 22 is an example of a body part identification device.

The endoscope 18 comprises an insertion section 24, which is to be inserted into a body cavity of a patient, and an operation unit 26 provided at a proximal end of the insertion section 24. the endoscope 18 is connected to the processor device 22 through a cord 28. The insertion section 24 comprises a distal portion 32, a flexible portion 34, and a flexible tube 36. The distal portion 32 incorporates an imaging unit 30. The flexible portion 34 bends to change a direction of the distal portion 32 (that is, an imaging direction of the imaging unit 30). The flexible tube 36 is flexible. The imaging unit 30 comprises an image sensor such as a CCD (charge coupled device), an objective lens, and a light window. The objective lens collects light onto the image sensor. The light window applies illumination light to a body part to be imaged. The imaging unit 30 captures an image of the body part located in an axial direction of the insertion section 24 and in front of the distal portion 32. The imaging unit 30 outputs image signals, which are generated by image capture, to the processor device 22.

Scale marks 40 are provided on an outer surface of the insertion section 24. The scale marks 40 are, for example, dots arranged at a predetermined pitch (for example, 1 cm) in a longitudinal direction of the insertion section 24. The scale marks 40 are used for detecting an amount (hereinafter referred to as the insertion amount) of insertion of the insertion section 24. The insertion amount indicates the length of the insertion section 24 inserted into the patient's body cavity. The insertion amount is, for example, an amount detected relative to the position of the mouthpiece 20. In other words, the insertion amount is the depth or the position of the distal portion 32 in the body cavity, relative to the position of the mouthpiece 20. A unit of the insertion amount is centimeter (cm), for example. The detection of the insertion amount will be described below.

Angle wires, a light guide, and a signal cable extend in the insertion section 24. The angle wires are used for bending the flexible portion 34. The light guide is composed of an optical fiber. The optical fiber transmits the illumination light from a light source to the light window. The signal cable transmits the image signals, which are outputted from the imaging unit 30, to the processor device 22, and transmits various signals (e.g. an instruction for imaging) from the processor device 22 to the imaging unit 30.

The operation unit 26 comprises a shutter button and an angle knob 42. The shutter button is operated to instruct still image capture. The angle knob 42 is operated (rotated) to wind up or draw the angle wires to bend the flexible portion 34. More specifically, the angle wire is wound up or drawn in accordance with an amount of the operation (an amount of the rotation) of the angle knob 42, to bend the flexible portion 34. In other words, in the endoscope 18, the bend amount of the flexible portion 34 is controlled in accordance with the amount of the operation of the angle knob 42.

The mouthpiece 20 has a tubular shape and is attached to the patient's mouth. The mouthpiece 20 keeps the patient's mouth open. The mouthpiece 20 helps the insertion section 24 to be inserted smoothly and prevents the insertion section 24 from being damaged (e.g. from being bitten by the patient's teeth). The insertion section 24 is inserted into the patient's body cavity through an opening of the mouthpiece 20.

The mouthpiece 20 is provided with small cameras 46 and 48. The cameras 46 and 48 are used to detect the insertion amount of the insertion section 24. Each of the cameras 46 and 48 comprises an image sensor such as a CCD. The cameras 46 and 48 capture images of the outer surface of the insertion section 24. Thereby the scale mark(s) 40 are imaged in the images captured by the cameras 46 and 48.

The cameras 46 and 48 are disposed in opposite positions with respect to the opening of the mouthpiece 20 such that the scale mark 40 is within at least one of imaging fields of the cameras 46 and 48 regardless of an amount (rotation amount) of the rotation of the insertion section 24, which is inserted through the mouthpiece 20 and rotated about an axis of the insertion section 24. In this embodiment, the camera 46 is disposed on a lower jaw side of the patient. The camera 48 is disposed on a nasal side of the patient. Thus the cameras 46 and 48 are opposed to each other.

The cameras 46 and 48 are connected communicably to the processor device 22 and controlled by the processor device 22. The cameras 46 and 48 start imaging in response to turning on the processor device 22. While the processor device 22 is on, the cameras 46 and 48 capture a movie at 30 frames per second, for example. Each captured frame is outputted as a camera image to the processor device 22. Based on the camera images, the processor device 22 counts the scale marks 40 passing through the mouthpiece 20. The scale marks 40 are arranged at the predetermined pitch, so that the insertion amount is detected by counting the scale marks 40 passing through the mouthpiece 20.

The processor device 22 has an imaging control function to input the instruction for imaging to the imaging unit 30 of the endoscope 18 to allow the imaging unit 30 to perform imaging. The processor device 22 has a display control function to generate a display image based on the image signals, which are outputted from the imaging unit 30, and to allow the display 72 to display the display image. The imaging unit 30 is able to perform movie capture and the still image capture. The movie capture is performed continuously while the processor device 22 is on, for example. The still image capture is performed in response to the instruction for imaging inputted from the shutter button of the operation unit 26.

The processor device 22 has a function (body part identification function) to identify a body part (hereinafter referred to as the imaged body part) imaged in a current image 49 (see FIG. 2), which is an image currently being captured by the imaging unit 30 of the endoscope 18. The processor device 22 is an example of a body part identification device.

Figure 2:
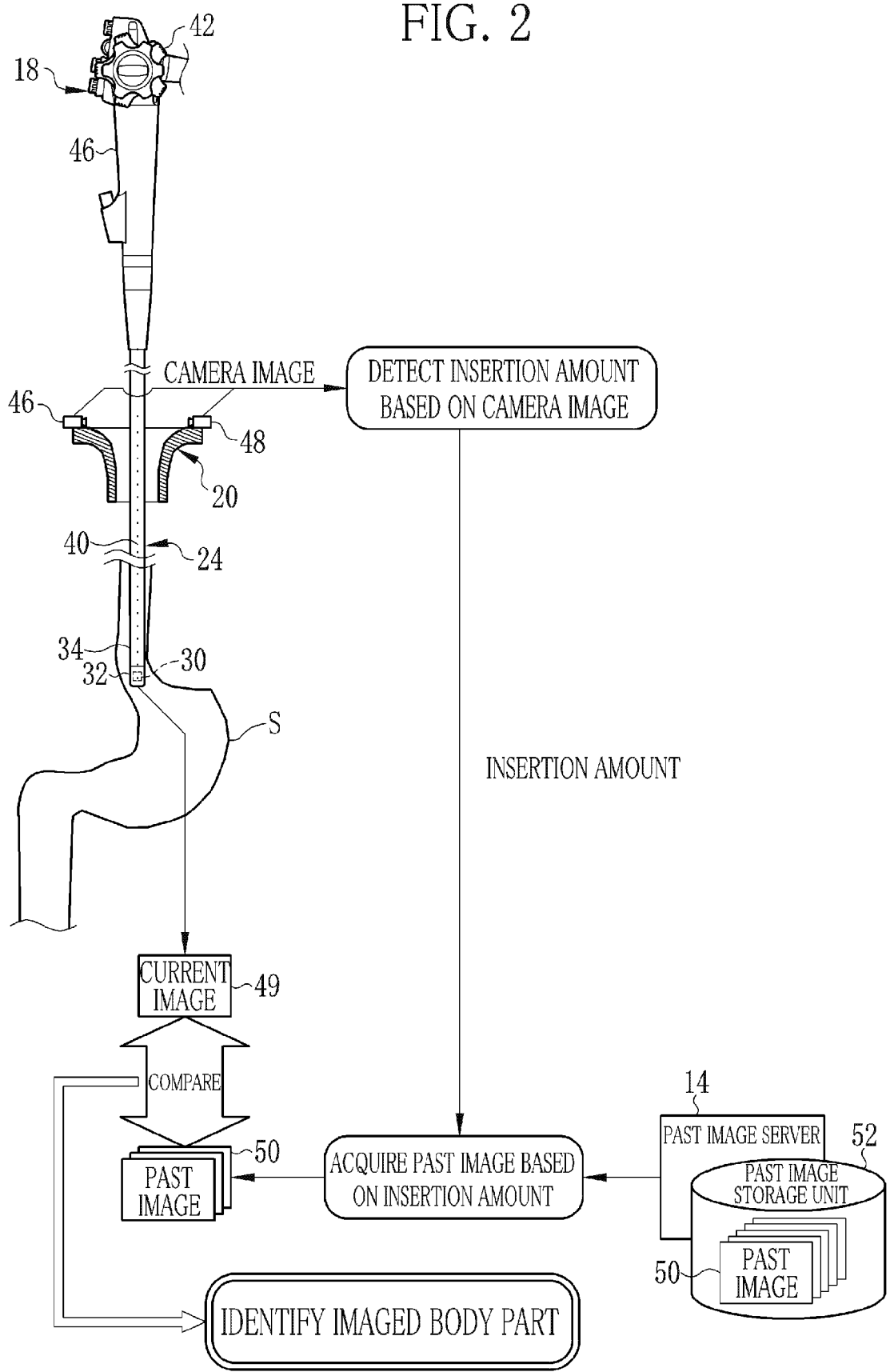
FIG. 2 is a schematic explanatory view illustrating a procedure for identifying an imaged body part.

As schematically shown in FIG. 2, the current image 49 is compared with past images 50, which are stored in the past image server 14, through pattern matching, to determine the past image 50 similar to the current image 49. Thereby the imaged body part is identified. The past images 50 are images captured in at least one past endoscopic examination. Each past image 50 stores imaged body part information as supplementary information. The imaged body part information is read from the past image 50 that is similar to the current image 49, and used to identify the imaged body part in the current image 49. It is considered that the images of the same body part have high similarity with each other. Hence the imaged body part in the current image 49 is identified by determining the past image 50 that has high similarity with the current image 49.

FIG. 2 shows that the distal portion 32 of the insertion section 24 has reached stomach S. In this case, the imaged body part in the current image 49 is "stomach" and the imaged body part in the past image 50 that has high similarity with this current image 49 is also "stomach". Through the comparison between the current image 49 and each of the past images 50, the past image 50 having high similarity with the current image 49 is determined. The imaged body part in the current image 49 is identified as "stomach" based on the imaged body part ("stomach") in the past image 50 that is determined to have high similarity with the current image 49.

The insertion amount is detected to narrow down the past images 50 that are to be compared with the current image 49. The plurality of past images 50 are stored in the past image server 14. The comparison between the current image 49 and each of the past images 50 in the past image server 14 takes much time to search for the past image 50 that is similar to the current image 49. To shorten the time for the comparison, the past images 50 are extracted based on the insertion amount. Thereby the number of the past images 50 to be compared with the current image 49 is narrowed down.

Here, the current image 49 may be a frame constituting the movie or the still image, which is captured in the still image capture. The purpose of identifying the imaged body part in the current image 49 is to notify a doctor (who is conducting the examination) of the imaged body part. For this reason, in a case of the movie, it is not necessary to identify the imaged body part in every frame. In this case, a process for identifying the imaged body part is executed on the frames at time intervals of one second, for example.

The past image server 14 comprises a past image storage unit 52, in which the plurality of past images 50 are stored. The past image server 14 is connected to the processor device 22 through the communication network 16. In response to a search request, which is inputted from the processor device 22, for searching for the past image(s) 50, the past image server 14 retrieves the requested past image(s) 50 from the past image storage unit 52 and transmits the retrieved past image(s) 50 to the processor device 22.

Figure 3:
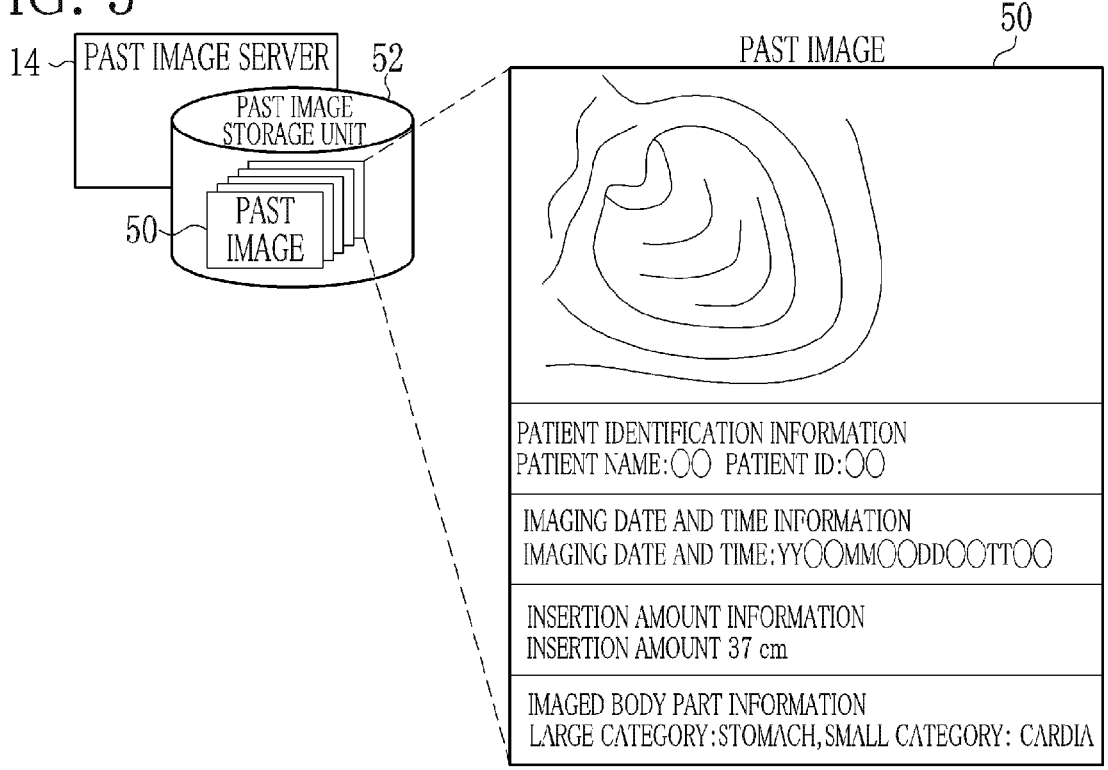
FIG. 3 is an explanatory view illustrating stored past images, to each of which supplementary information is attached.

As illustrated in FIG. 3, each past image 50 stored in the past image storage unit 52 stores the supplementary information attached to the image data. The supplementary information includes various types of information such as patient identification information (e.g. a patient name, a patient ID, or the like) for identifying a patient of interest, imaging date and time information representing the date and time of the imaging, insertion amount information representing the insertion amount, and the imaged body part information representing the imaged body part. The patient of interest is a patient who is the subject of the examination or being imaged in the current image 49.

The past image 50 is an image captured in a past examination by using an endoscope apparatus having a function of detecting an insertion amount and a function of identifying an imaged body part. These functions are similar to or the same as those of the endoscope apparatus 12 described in this embodiment. The endoscope apparatus 12 records the detected insertion amount and the identified imaged body part as the supplementary information on the current image 49 used for identifying the imaged body part. In other words, the insertion amount of the insertion section 24 at the time the current image 49 is captured and the body part identified based on the insertion amount are recorded as the supplementary information in real time on the current image 49. The patient identification information is also recorded as the supplementary information on the current image 49.

As described above, the current image 49 is the frame of the movie or the still image. All or a part of the current images 49 are recorded and stored as the past images 50 in the past image storage unit 52. Hence the past image storage unit 52 stores the past images 50, on each of which the insertion amount information, the imaged body part information, and the patient identification information are recorded as the supplementary information.

The imaged body part information is information representing an imaged body part. For example, in a case where the subject of the examination is the upper gastrointestinal tract, the imaged body part information is information representing an organ such as esophagus, stomach, or duodenum. The imaged body part information may include information of an imaged body part of a small category, into which a large category (in this example, an organ) is subdivided. For example, the imaged body part of the small category may be a part of the stomach such as cardia, gastric angle, or pylorus in a case where the imaged body part of the large category is the stomach. The more the body part information is subdivided or segmented, the more accurate the identification of the imaged body part becomes.

Figure 4:
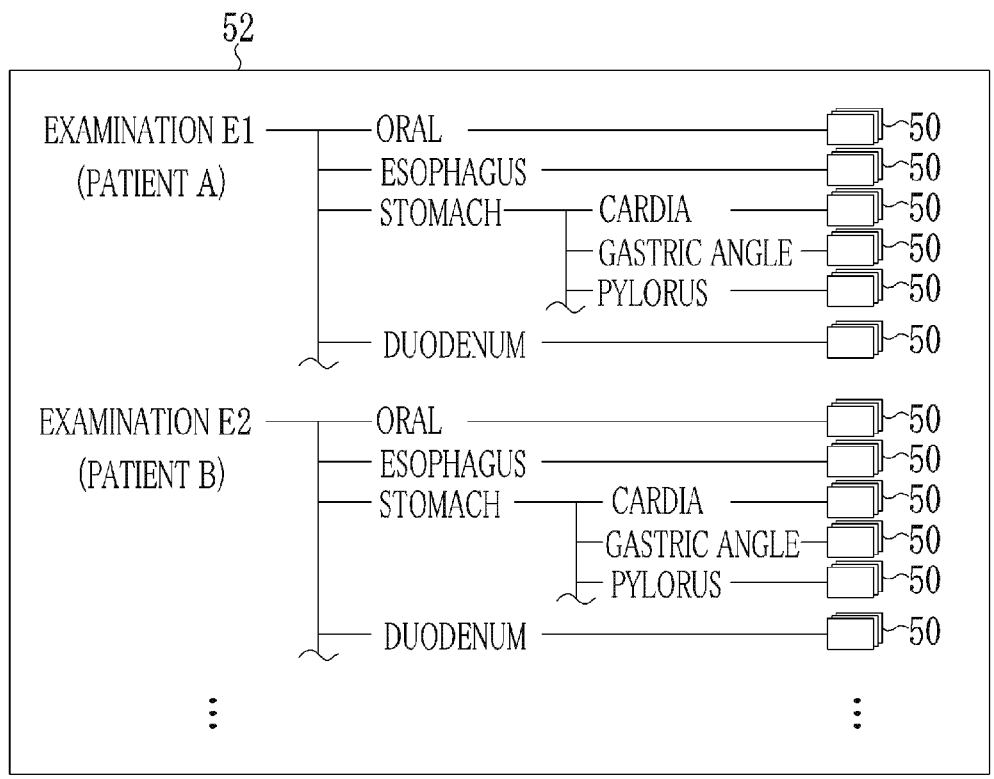
FIG. 4 is an explanatory view illustrating the stored past images classified according to the examination.

As illustrated in FIG. 4, the past image storage unit 52 stores the two or more past images 50 for each examination E (e.g. for each of an examination E1, an examination E2, and so forth). Supplementary information such as the imaged body part information is recorded on each of the past images 50. In this example, the examinations E1 and E2 are performed on the different patients A and B, respectively. Alternatively, the examination E may be performed two or more times on the same patient. In this case, the past images 50 captured in the examinations E that are performed on the same patient are stored in the past image storage unit 52. In this example, the examinations E1 and E2 are the examinations of the upper gastrointestinal tract. The past images 50 captured in each of the examinations E1 and E2 include the past images 50 of the imaged body part such as inner mouth (corresponding to "oral" in the drawings), the esophagus, or the stomach. The past images 50 to be used for the comparison with the current image 49 are extracted from the past image storage unit 52.

Figure 5:
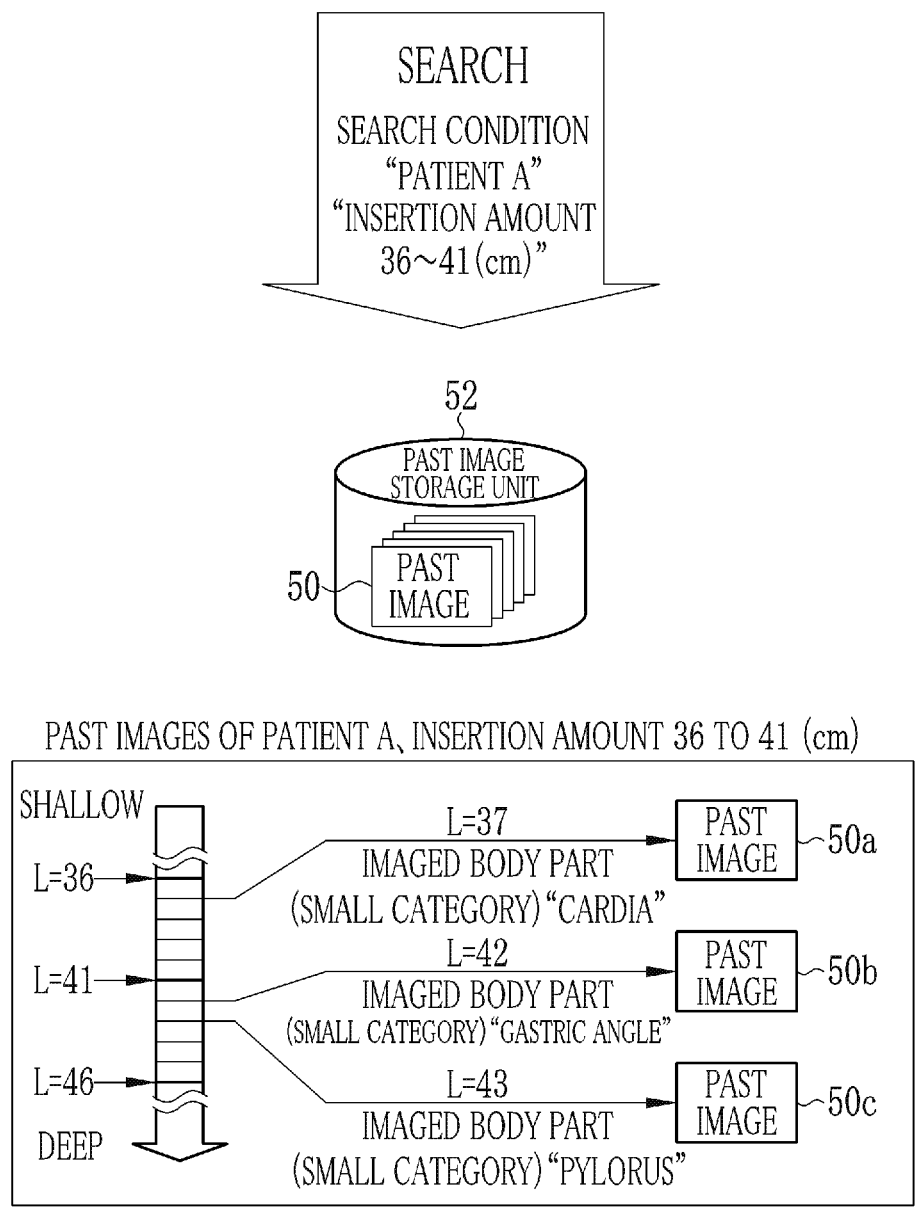
FIG. 5 is an explanatory view illustrating an example of a search for the past images.

As illustrated in FIG. 5, the past image storage unit 52 is a database in which the past image 50 is searched for based on a search condition such as the patient identification information, the insertion amount information, and/or the imaged body part information described above. For example, the past image 50 is searched for by designating the search condition (e.g. the patient identification information and the insertion amount information). Thereby the past image storage unit 52 extracts the past image(s) 50 that matches the search condition.

In an example illustrated in FIG. 5, a patient A is designated as the patient identification information. A range of 36 to 46 cm is designated as an insertion amount L. Thereby past images 50a to 50c are extracted by the search. The past image 50a is a past image of the imaged body part "cardia" captured at a position corresponding to the insertion amount L of 37 cm. The past image 50b is a past image of the imaged body part "gastric angle" captured at a position corresponding to the insertion amount L of 42 cm. The past image 50c is a past image of the imaged body part "pylorus" captured at a position corresponding to the insertion amount L of 43 cm.

As described above, the past image server 14 is able to search for the past image 50 of the imaged body part corresponding to the specific insertion amount L. Thus, the past image server 14 extracts the past image(s) 50 captured at the insertion amount(s) L similar to that of the current image 49.

The patient identification information is used as the search condition. Thereby the past image(s) 50 of the same patient as in the current image 49 is extracted. The past image 50 is compared with the current image 49 to identify the imaged body part in the current image 49. In a case where the past images 50 of the same patient of interest as in the current image 49 are used, the extracted past image 50 has higher similarity with the current image 49 than the past image 50 extracted from the past images 50 of another patient different from the patient of interest imaged in the current image 49. Thus the accuracy in identifying the imaged body part is improved.

Figure 6:
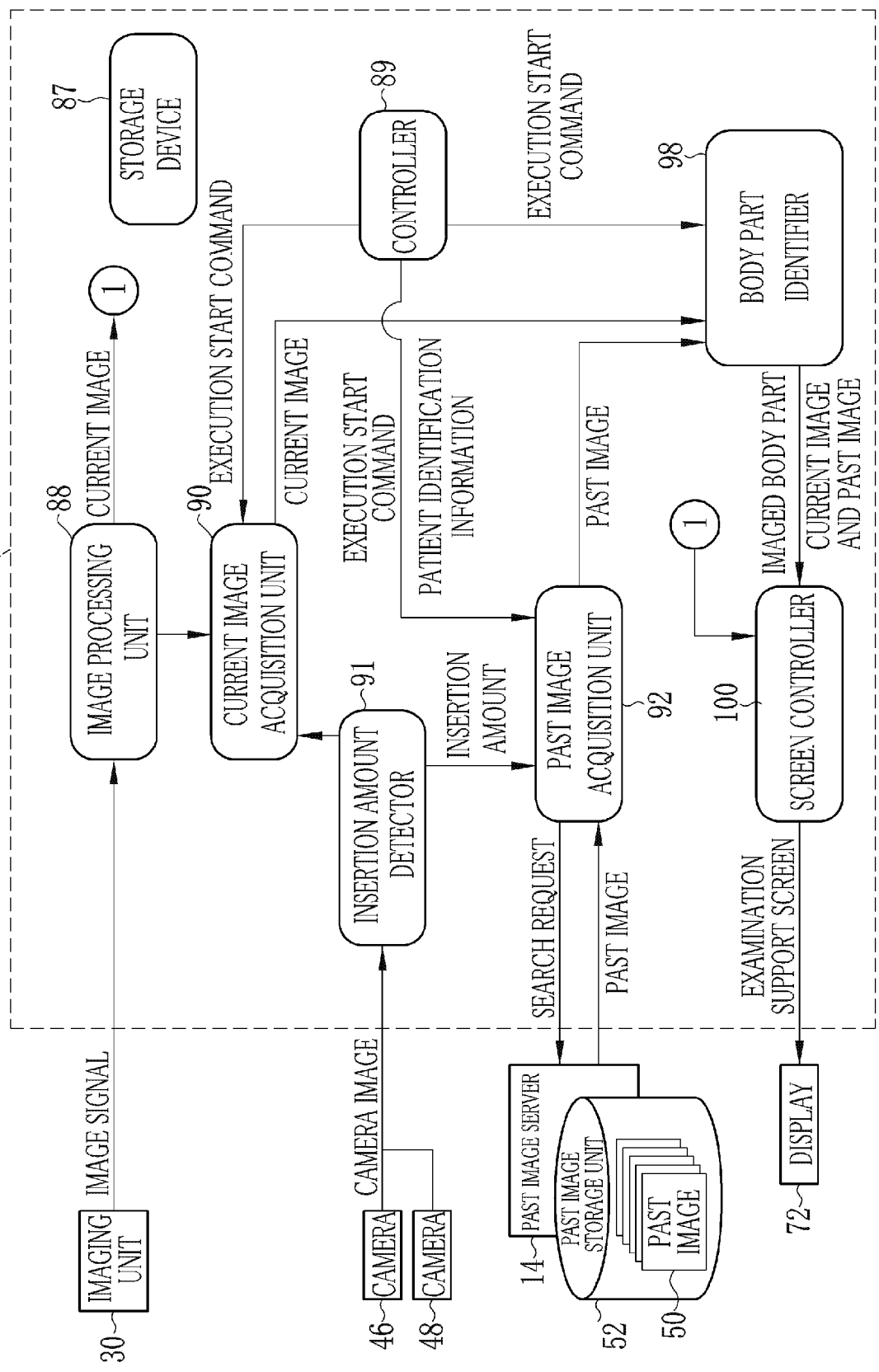
FIG. 6 is an explanatory view schematically illustrating functions of a processor device.

As illustrated in FIG. 6, the processor device 22 comprises an image processing unit 88, a controller 89, a current image acquisition unit 90, a insertion amount detector 91, a past image acquisition unit 92, a body part identifier 98, a screen controller 100, and a storage device 87.

The image processing unit 88 performs image processing on the image signals outputted from the imaging unit 30, to generate an observation image. The image processing unit 88 outputs the observation image as the current image 49. The current image 49 is inputted to the screen controller 100 and displayed on the display 72. The screen controller 100 executes a process (display image generation process) for generating the display image and a process (display control process) for displaying the display image and then outputs the display image (the current image 49) to the display 72. Thereby the current image 49 is displayed on the display 72 in real time to be observed by the doctor.

During the movie capture, the image signals of the frames, which constitute the movie, are inputted at predetermined time intervals from the imaging unit 30 to the image processing unit 88. Based on the image signals of the respective frames, the image processing unit 88 generates the current images 49 and outputs the current images 49 sequentially to the screen controller 100. In a case where the shutter button is operated, the image signals of the still image are inputted from the imaging unit 30 to the image processing unit 88. The image processing unit 88 generates the current image 49 (the still image) and outputs the current image 49 to the screen controller 100. The current images 49 (the movie and the still image) are stored in the storage device 87 such as a memory or a hard disk drive.

The controller 89 centrally controls each section of the processor device 22. The controller 89 issues an execution start command for a body part identification process, to control each of the current image acquisition unit 90, the past image acquisition unit 92, and the body part identifier 98. During the movie capture, the execution start command is issued at the time intervals of one second as described above. In a case of the still image capture, the execution start command is issued at the timing of capturing the still image. In response to the input of the execution start command to each section, the body part identification process, which is a process for identifying the imaged body part, starts. The controller 89 inputs the patient identification information, which is used as the search condition for the search of the past image(s) 50, to the past image acquisition unit 92. For example, the patient identification information is included in an examination order inputted to the processor device 22 before the start of the examination. The controller 89 reads the patient identification information from the examination order and inputs the patient identification information to the past image acquisition unit 92.

In response to the input of the execution start command, the current image acquisition unit 90 acquires the current image 49 that is outputted from the image processing unit 88 at the timing of the input of the execution start command. In response to the input of the execution start command from the controller 89, the current image acquisition unit 90 outputs the acquired current image 49 to the body part identifier 98.

The camera images captured by the cameras 46 and 48 are inputted in real time to the insertion amount detector 91. The insertion amount detector 91 sequentially analyzes the inputted camera images. Based on a result of the analysis, the insertion amount detector 91 detects the insertion amount of the insertion section 24. To be more specific, the outer surface of the insertion section 24 with the scale marks 40 are imaged in the camera image. As the insertion section 24 is inserted into the patient's body cavity, the insertion section 24 moves relative to the mouthpiece 20. With the move of the insertion section 24, the scale marks 40 (that is, the dots in this example) sequentially pass through the position between the cameras 46 and 48.

The insertion amount detector 91 counts the number of the dots of the scale marks 40 imaged in each of the sequentially inputted camera images. Thereby the insertion amount detector 91 detects the insertion amount. For example, the insertion amount represents an amount (in centimeters) of the insertion of the distal end of the insertion section 24 relative to the mouthpiece 20. Alternatively, note that the scale marks 40 may be numbers each representing an insertion amount. The insertion amount may be detected by reading (detecting) the number from the camera image.

In response to the input of the execution start command, the current image acquisition unit 90 and the past image acquisition unit 92 acquire the insertion amount, which is outputted from the insertion amount detector 91, at the timing of the input of the execution start command. In response to the input of the execution start command, the past image acquisition unit 92 acquires the past image(s) 50, which is used for identifying the imaged body part, from the past image server 14. To be more specific, the past image acquisition unit 92 transmits the search request to the past image server 14. In the search request, the insertion amount, which is acquired from the insertion amount detector 91, at the timing of the input of the execution start command and the patient identification information, which is acquired from the controller 89, are designated as the search condition.

The insertion amount designated as the search condition is set to be a predetermined range including the insertion amount inputted from the insertion amount detector 91. For example, in this embodiment, the insertion amount is set to be a range of 10 cm around the inputted insertion amount (the central value). The range including the insertion amount is designated as the search condition to allow for the detection error of the insertion amount. For example, the insertion amounts for observing the stomach are not completely the same between the past and current examinations even if the same body part (the stomach in this example) is observed in two or more examinations performed on the same patient. This is because the organ (e.g. the stomach) extends or shrinks. For this reason, the predetermined range including the detected insertion amount is designated as the search condition.

Upon receiving the search request, the past image server retrieves the past image(s) 50 that matches the search condition, which is designated by the search request, and transmits the retrieved past image(s) 50 to the past image acquisition unit 92. Thus, the past image acquisition unit 92 acquires the past image(s) 50 from the past image server 14. Thus, the past image(s) 50 corresponding to the designated insertion amount is extracted.

The insertion amount designated as the search condition is not the insertion amount L itself, which is detected by the insertion amount detector 91, but the predetermined range around the insertion amount L (the central value). For example, as illustrated in FIG. 5, in a case where the current insertion amount L detected by the insertion amount detector 91 is 41 cm, a range of 10 cm around the insertion amount L (=41 cm) (the central value), that is, the range of 36 to 46 cm is designated as the search condition. Hence the past images 50*a* to 50*c* having the insertion amounts within this range are acquired (see FIG. 5). The past image acquisition unit 92 outputs the past images 50 (the past image 50*a* to 50*c* in this example) thus acquired to the body part identifier 98.

In response to the input of the execution start command from the controller 89, the body part identifier 98 compares the current image 49, which is inputted from the current image acquisition unit 90, with each of the past images 50, which are inputted from the past image acquisition unit 92. The body part identifier 98 performs, for example, well-known pattern matching determination, in which a contour, a color, or the like is compared, to calculate the similarity between the current image 49 and each of the past images 50. Among the past images 50, the body part identifier 98 determines the past image 50 having the highest similarity with the current image 49. The body part identifier 98 reads the imaged body part information from the past image 50 having the highest similarity with the current image 49 and determines the imaged body part that is represented by the imaged body part information of the past image 50 to be the imaged body part in the current image 49.

More specifically, a method for calculating the similarity by comparing the current image 49 with the past image 50 is performed as follows. First, a feature quantity such as a shape or a color is extracted from blood vessel structure in mucosa or from ductal structure in mucosal surface in each of the current image 49 and the past image 50. Next, the similarity is calculated by comparing the feature quantity of the current image 49 with the feature quantity of the past image 50. These processes are executed on each of the past images 50 to calculate the similarity between the current image 49 and each of the past image 50. The past image 50 having the highest similarity with the current image 49 is determined among the past images 50.

After the feature quantity is extracted from each of the past images 50 and the current image 49 and before calculating the similarity between each of the past images 50 inputted from the past image acquisition unit 92 and the current image 49, filtering may be performed to narrow down the past images 50 that are to be used for calculating the similarity. This is because the mucosa (e.g. corrugation or the like of the mucosa) displayed looks different in color and shape according to an organ (e.g. the esophagus, the stomach, or the like). The difference in the displayed mucosa is caused by a difference in feature quantity. There is a high possibility that the images with different feature quantities show different organs. For this reason, after the feature quantity of each of the past images 50 and the current image 49 is extracted, the past image 50 having the feature quantity significantly different from that of the current image 49 may be eliminated from the past images 50 that are to be compared with the current image 49.

The body part identifier 98 outputs information of the identified imaged body part to the screen controller 100. Along with the information of the identified imaged body part, the body part identifier 98 outputs the current image 49 used for the identification of the imaged body part and the past image 50 that is determined to have the highest similarity with the current image 49, to the screen controller 100.

Based on the information of the identified imaged body part, the current image 49 used for the identification of the imaged body part, and the past image 50 that is determined to have the highest similarity with the current image 49, the screen controller 100 generates an endoscopic examination support screen (hereinafter simply referred to as the examination support screen) 102 (see FIG. 7) and controls a display of the examination support screen 102 on the display 72. Thus, the screen controller 100 functions as an image generator for generating the examination support screen 102 and functions also as a display controller for controlling the display of the examination support screen 102.

Figure 7:
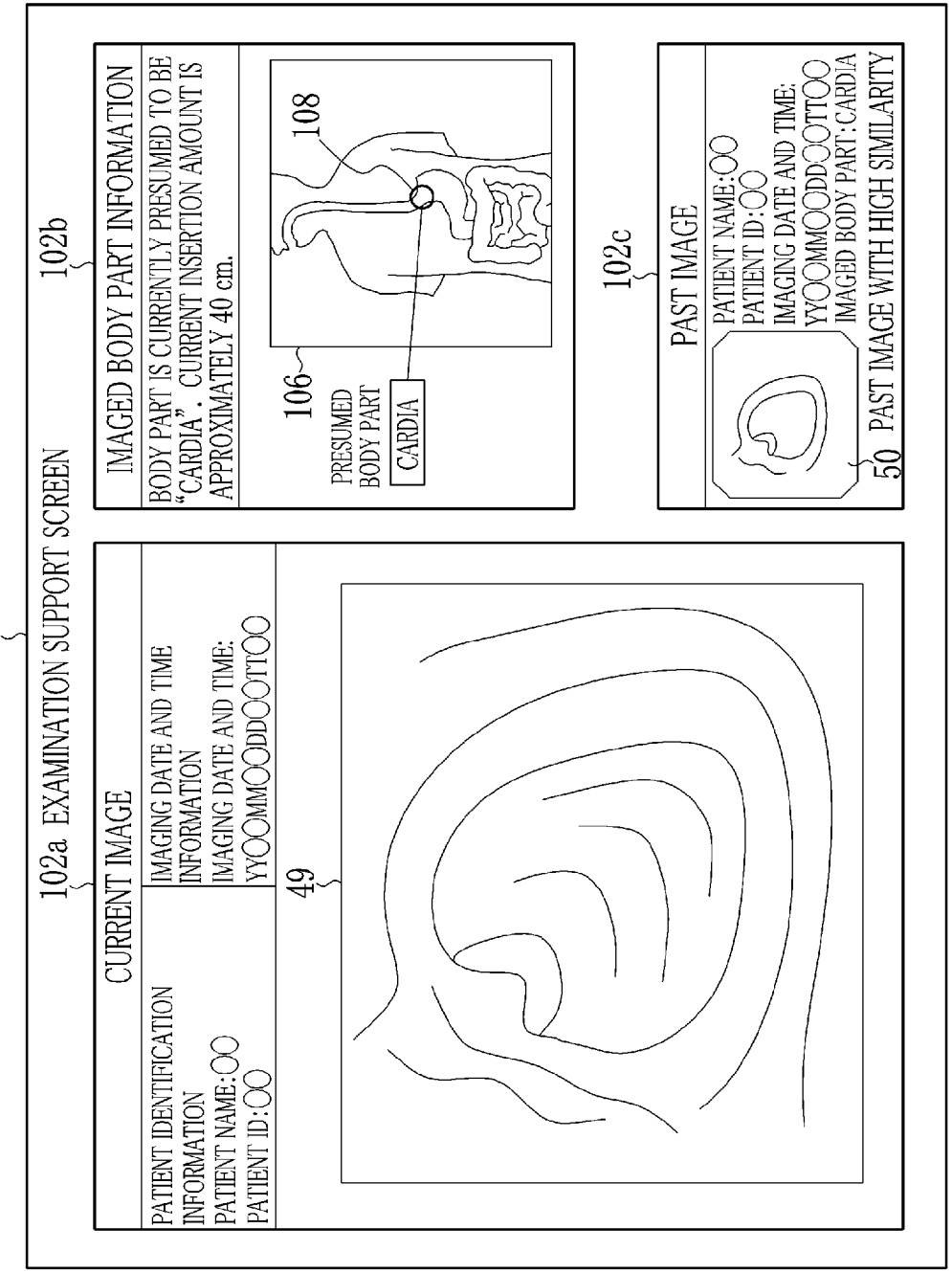
FIG. 7 is an explanatory view illustrating an endoscopic examination support screen.

As illustrated in FIG. 7, the examination support screen 102 comprises a current image display area 102*a*, a body part display area 102*b*, and a past image display area 102*c*. The current image display area 102*a* displays the current image 49, the patient identification information of the patient being imaged in the current image 49, and the imaging date and time information of the current image 49. The body part display area 102*b* displays the identified imaged body part, which is identified by the body part identifier 98, of the current image 49. The body part display area 102*b* also displays the insertion amount information acquired at the time of imaging the current image 49.

The current image 49 is successively updated on the examination support screen 102 during the movie capture. The imaged body part information and the past image 50 that is used for identifying the imaged body part are updated at the same time intervals as the execution of the body part identification process. In a case where the still image is captured, in other words, in the case where the current image 49 is the still image, the still image is displayed, interrupting the display of the movie.

In this embodiment, the identified imaged body part is displayed as text information. In addition, a circular mark 108 is provided on a schema image 106, which represents a human body. Thereby the identified imaged body part is displayed also as image information.

Of the past images 50 compared with the current image 49 in identifying the imaged body part, the past image 50 having the highest similarity with the current image 49 is displayed in the past image display area 102c. The past image display area 102c also displays the patient identification information and the imaging date and time information of the displayed past image 50. Thus, the past image 50 used for the identification of the imaged body part is displayed to enable verification of the past image 50 used.

Figure 8:
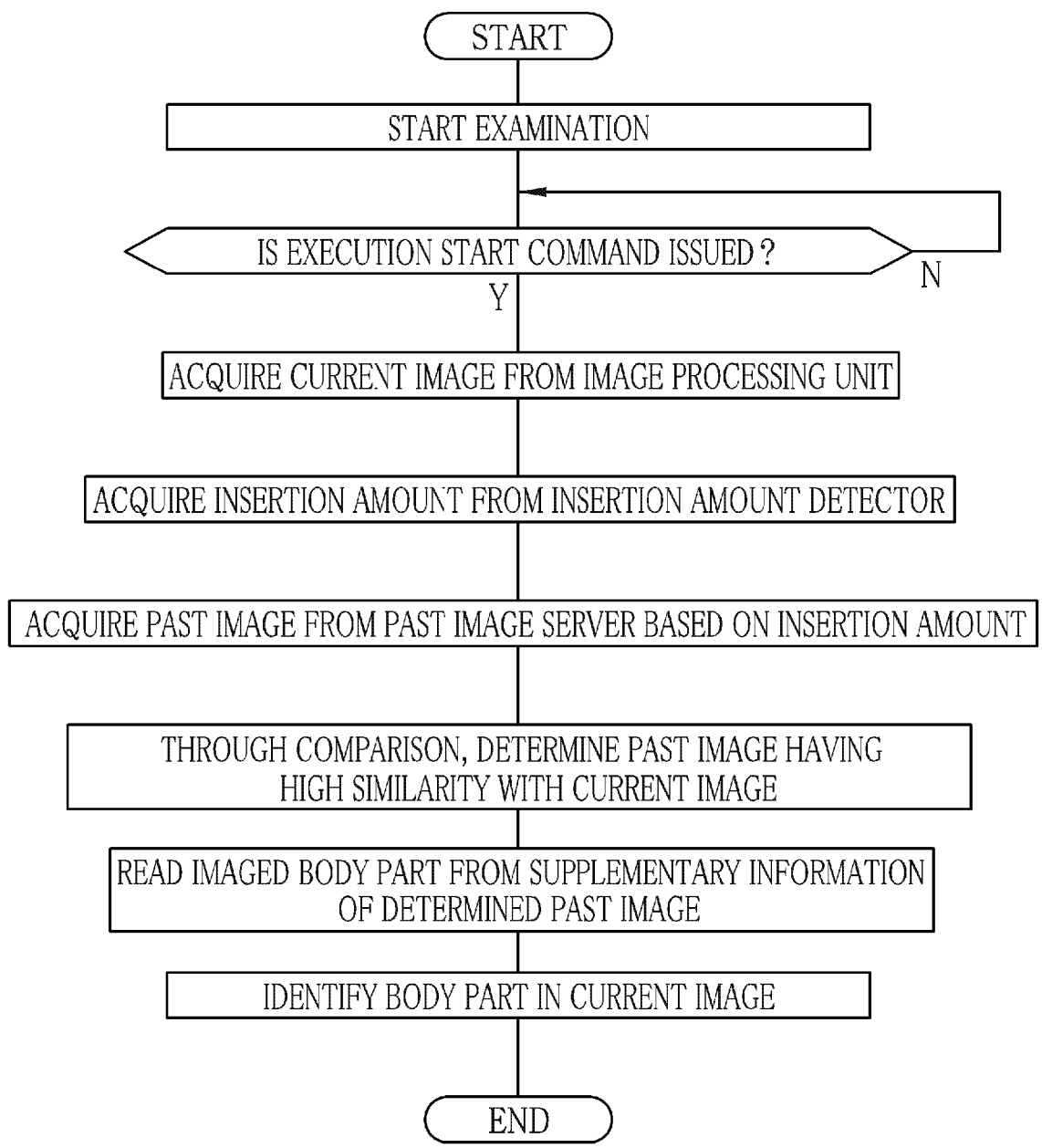
FIG. 8 is a flowchart illustrating a procedure for identifying the imaged body part.

Hereinafter, referring to a flowchart in FIG. 8, an operation of the above configuration is described. The endoscope apparatus 12 starts capturing the movie upon the start of the examination. In the processor device 22, the image processing unit 88 generates the current image 49 based on the image signals from the imaging unit 30. The screen controller 100 displays the current image 49 on the display 72. The still image is captured by operating the shutter button of the operation unit 26. The body part imaged in the current image 49 changes with the insertion amount of the insertion section 24. Thus the current image 49, which shows the imaged body part corresponding to the insertion amount of the insertion section 24, is observed.

Based on the camera images captured by the cameras 46 and 48, the insertion amount detector 91 detects the insertion amount of the insertion section 24 of the endoscope 18.

The controller 89 issues the execution start command for the body part identification process at the predetermined time intervals during the movie capture. In the case of the still image capture, the controller 89 issues the execution start command in response to capturing the still image. The execution start command is outputted to each of the current image acquisition unit 90, the past image acquisition unit 92, and the body part identifier 98.

In response to the input of the execution start command, the current image acquisition unit 90 acquires the current image 49 outputted from the image processing unit 88. In response to the input of the execution start command, the past image acquisition unit 92 acquires the insertion amount detected by the insertion amount detector 91. The past image acquisition unit 92 transmits the search request to the past image server 14. The search request designates the patient identification information and the predetermined range including the detected insertion amount as the search condition. The past image server 14 retrieves the past image(s) 50 that matches the search condition and transmits the retrieved past image(s) 50 to the past image acquisition unit 92. Since the past image(s) 50 is acquired based on the insertion amount, the imaged body part in the extracted past image(s) 50 is located in a range close to the insertion amount corresponding to the imaged body part of the current image 49.

The extracted past images 50 and the current image 49 are inputted to the body part identifier 98. The body part identifier 98 compares the current image 49 with each of the extracted past images 50 and calculates the similarity between the current image 49 and each of the past images 50. The body part identifier 98 determines the past image 50 having the highest similarity with the current image 49 and reads the imaged body part information of the past image 50 with the highest similarity. Here, the imaged body part information represents the imaged body part in the past image 50 with the highest similarity. The body part identifier 98 determines the imaged body part in the past image 50 to be the imaged body part in the current image 49.

The screen controller 100 generates the examination support screen 102 (see FIG. 7) based on the identified imaged body part, the past image 50 used for identifying the imaged body part, the current image 49, and the insertion amount corresponding to the current image 49. The examination support screen 102 is displayed on the display 72. Thereby the doctor who is conducting the examination is informed of the imaged body part of the current image 49.

During the movie capture, the current image 49 is successively updated on the examination support screen 102. The execution start command is issued at the time intervals of one second. In response to this, the body part identification process is executed at the same time intervals as the execution start command. The imaged body part information is updated at the time intervals of approximately one second. In the case of the movie, the imaged body part of the current image 49 successively changes with a change in the insertion amount of the insertion section 24. Since the imaged body part information is updated at the time intervals of approximately one second, the update of the imaged body part information keeps up with the change in the current image 49 being displayed. The body part identification process may be executed at the time intervals of more or less than one second.

The imaged body part information and the past image 50 used for identifying the imaged body part are updated at the same time intervals as the execution of the body part identification process. In the case where the still image is captured, the captured still image is displayed as the current image 49, interrupting the movie being displayed. The imaged body part information and the past image 50 corresponding to the still image (that is, the current image 49) are displayed while the still image is displayed. Alternatively, both of the movie and the still image may be displayed at a time on the examination support screen 102. Thereby both of the movie and the still image are observed at a time.

The body part identifier 98 records each of the insertion amount information, which represents the insertion amount, and the imaged body part information, which represents the identified imaged body part, as the supplementary information on the current image 49 on which the body part identification process has been executed. Thereby, in the case where the current image 49 is stored as the past image 50, the past image 50 stores the insertion amount information and the imaged body part information.

In the case of the movie capture described in this embodiment, the body part identification process is executed at the time intervals of, for example, few seconds, so that the insertion amount information and the imaged body part information are recorded on each frame acquired at the time intervals of few seconds. In the case where the current image 49 is the still image, the insertion amount information and the imaged body part information are recorded on each still image. All or a part of the movie and the still image captured as the current images 49 are stored and used as the past images 50.

As described above, in the embodiments of the present invention, the past images 50 are acquired based on the insertion amount. The current image 49 is compared with each of the past images 50 to determine the past image 50 similar to the current image 49. Thus the imaged body part of the current image 49 is determined. The accuracy in identifying the imaged body part is higher in the embodiments of the present invention than in those of Japanese patent No. 4262741 and US2015/0208947, which describe apparatuses for identifying the imaged body part based on the insertion amount of the insertion section, the bend amount of the insertion section (the flexible portion), the rotation amount of the insertion section about the axis, and the like. It is considered that the insertion amount, the bend amount, and the rotation amount have a high amount of detection errors. High identification accuracy is ensured by the comparison using the image analysis such as the pattern matching. In the embodiments of the present invention, the insertion amount is used only to narrow down the past images 50 that are to be compared with the current image 49. Hence the insertion amount does not affect the identification accuracy even if the insertion amount has an error. Narrowing down the past images 50 by the insertion amount shortens the processing time.

According to the embodiments of the present invention, the current image 49 is compared with the past image 50 to improve the accuracy in identifying the imaged body part. Hence the accuracy in identifying the imaged body part is improved easily without using a large-scale apparatus, as compared with a conventional technique in which the accuracy in identifying the imaged body part is improved by using 3-dimensional image data acquired through a CT examination or an MRI examination as described in, for example, Japanese Patent Laid-Open Publication No. 2012-165838.

In this embodiment, the current image 49 and the past image 50 of the same patient are compared with each other. The similarity between the current image 49 and the past image 50 of the same patient is higher than the similarity between the current image 49 and the past image 50 of different patients even if the imaged body part is the same. Hence the comparison between the current image 49 and the past image 50 of the same patient enables the extraction of the past image 50 having high similarity with the current image 49. As a result, the accuracy in identifying the body part is further improved.

In this embodiment, as illustrated in FIG. 7, the mark 108 indicating the identified imaged body part is provided on the schema image. Thereby the identified imaged body part is displayed as text information and image information (see FIG. 7). This makes it easy for a user to perceive the imaged body part.

In this embodiment, as illustrated in FIG. 7, the current image 49 and the past image 50 that is determined to have imaged the same body part as in the current image 49 are displayed in a comparable manner. The current image 49 is visually compared with the past image 50 to verify whether the identified imaged body part is correct.

Second Embodiment

In the above embodiment, the current image 49 and the past image 50 of the same patient (the same patient of interest) are used for the comparison. Instead, the past image 50 of a patient (another patient) different from the patient of interest may be used to identify the imaged body part.

The comparison between the current image 49 and the past image 50 of different patients results in similarity lower than that in the comparison between the current image 49 and the past image 50 of the same patient (the same patient of interest) even if the imaged body part is the same. However, in a case where the past image server 14 does not contain the past image 50 of the same patient as in the current image 49, the current image 49 cannot be compared with the past image 50 of the same patient. In this case, it is effective to use the past image 50 of another patient for the comparison with the current image 49 of the patient of interest.

Figure 9:
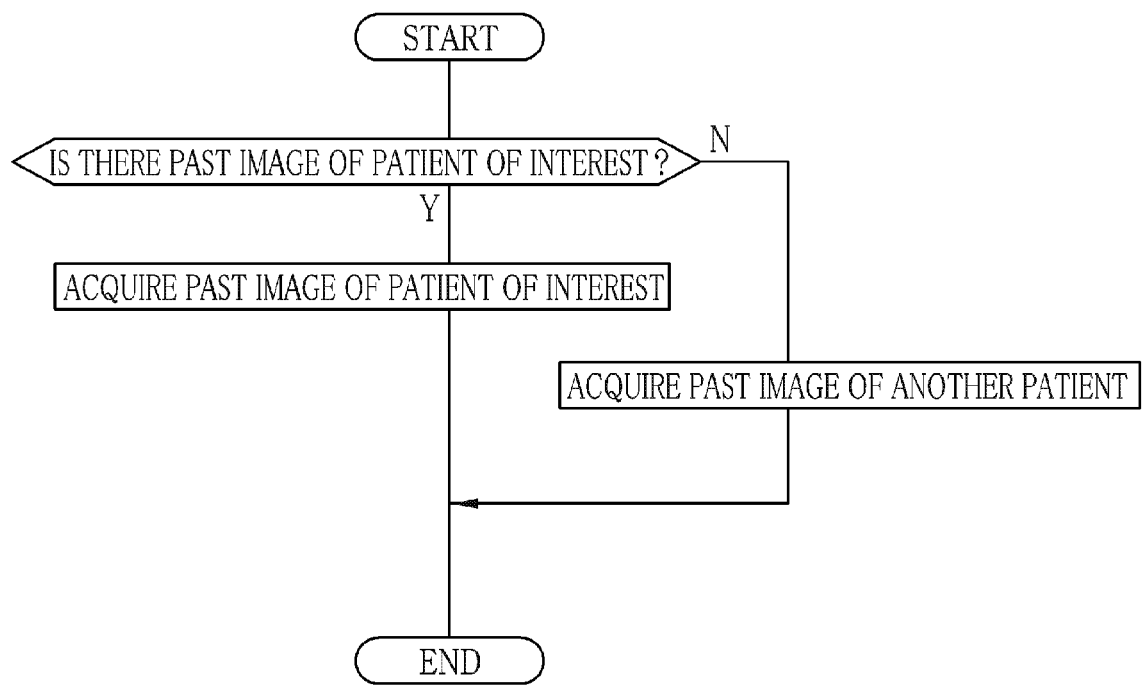
FIG. 9 is an explanatory view illustrating an example in which the past images to be compared with a current image are selected depending on the presence or absence of the past images of a patient of interest.

As illustrated in FIG. 9, it is preferred that the past image acquisition unit 92 acquires the past image(s) 50 of the patient of interest in the case where the past image storage unit 52 contains the past image(s) 50 of the patient of interest. It is preferred that the past image acquisition unit 92 acquires the past image(s) 50 of another patient different from the patient of interest in the case where the past image storage unit 52 does not contain the past image(s) 50 of the patient of interest.

Third Embodiment

Figure 10:
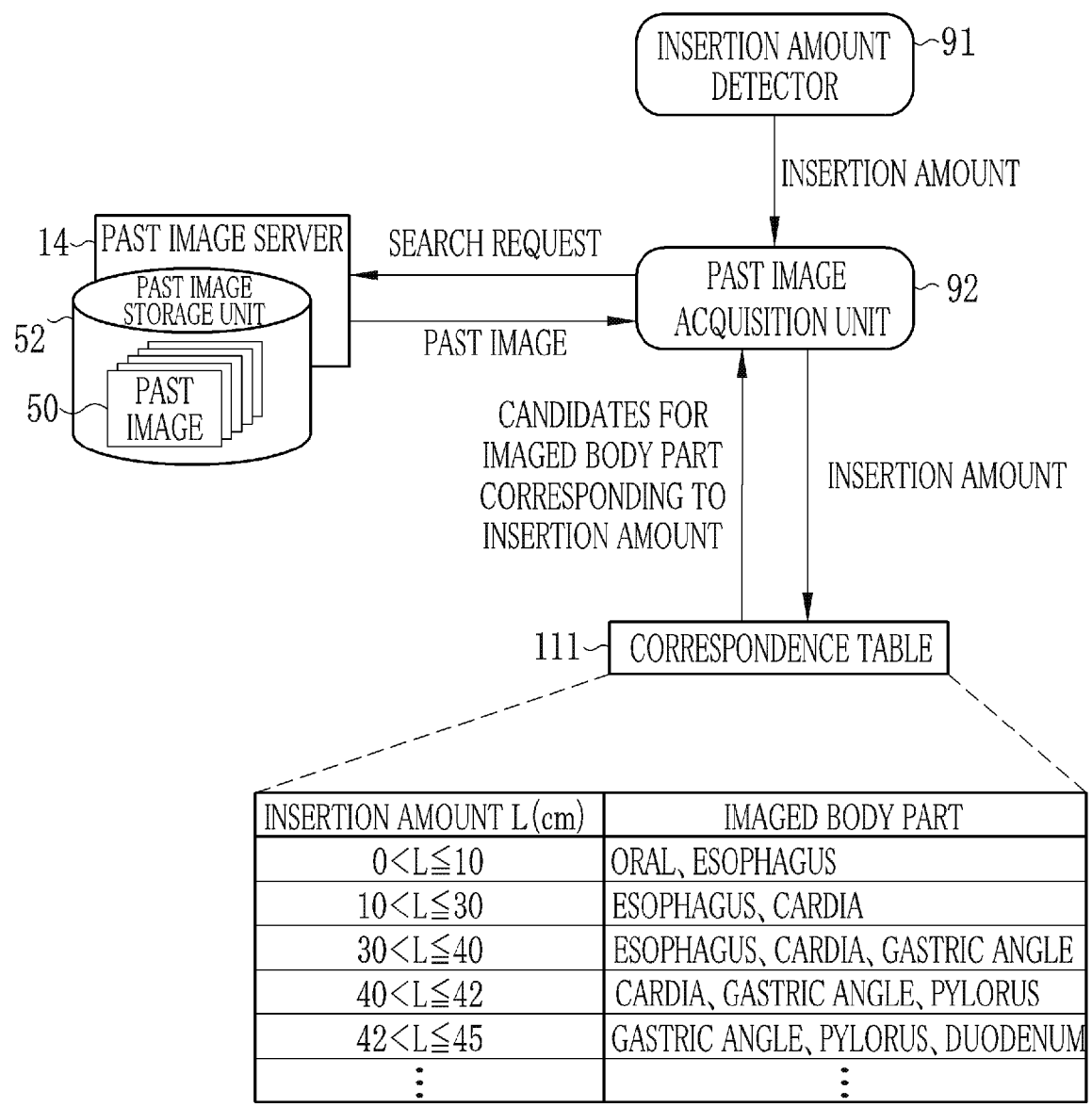
FIG. 10 is an explanatory view illustrating an example in which a correspondence table is used to narrow down the past images to be compared with the current image.

An example of a third embodiment illustrated in FIG. 10 uses a correspondence table 111, which stores the correspondence between the insertion amounts and the candidates for the imaged body part. In the first embodiment, the insertion amount itself is used as a search condition (search keyword) to retrieve the past image 50. In the third embodiment, first, the past image acquisition unit 92 refers to the correspondence table 111, to determine the candidates for the imaged body part based on the detected insertion amount. The past image acquisition unit 92 designates the candidates for the imaged body part as the search condition, to acquire the past images 50 corresponding to the candidates for the imaged body part from the past image storage unit 52.

There is a certain correspondence between the insertion amount and the imaged body part. The correspondence table 111 stores the correspondence between the range of the insertion amount and the candidate for the imaged body part corresponding to the range of the insertion amount. In an example in FIG. 10, the insertion amount is denoted by L (cm). A range "0<L≤10" of the insertion amount corresponds to the imaged body parts "oral (inner mouth)" and "esophagus". A range "10<L≤30" of the insertion amount corresponds to the imaged body parts "esophagus" and "cardia". A range "30<L≤40" corresponds to the imaged body parts "esophagus", "cardia", and "gastric angle". A range "40<L≤42" corresponds to the imaged body parts "cardia", "gastric angle", and "pylorus". A range "42<L≤45" corresponds to the imaged body parts "gastric angle", "pylorus", and "duodenum".

For example, in the case where the detected insertion amount L is 36 cm, the past image acquisition unit 92 refers to the correspondence table 111 and determines "esophagus", "cardia", and "gastric angle" to be the candidates for the imaged body part. The past image acquisition unit 92 acquires the past image(s) 50 with the supplementary information having the imaged body part information corresponding to the "esophagus", "cardia", and "gastric angle". In this example, the imaged body part information is used as the search condition, so that the supplementary information of the past image 50 may include only the imaged body part information. The insertion amount information is unnecessary.

The correspondence table 111 allows the use of the past image 50 with the supplementary information having only the imaged body part information. The supplementary information of the past image 50 may be automatically inputted by the endoscope apparatus as described in the first embodiment or, alternatively, manually inputted. In the case where the supplementary information is inputted manually, it is difficult to record the insertion amount information. With regard to the imaged body part information, for example, the doctor may identify the imaged body part while observing the past image 50 and may input the imaged body part information of the identified imaged body part as the supplementary information of the past image 50. The method using the correspondence table 111 is effective in a case where the insertion amount information cannot be recorded on the past image 50.

Note that the correspondence between the insertion amounts and the candidates for the imaged body part in the correspondence table 111 are determined based on standard values of adult, for example. However, such correspondence may vary according to gender, body shape, or the like among the adults. For this reason, two or more reference tables corresponding to the genders, the body shapes, or the like of the patients may be provided and selectively used.

Fourth Embodiment

Figure 11:
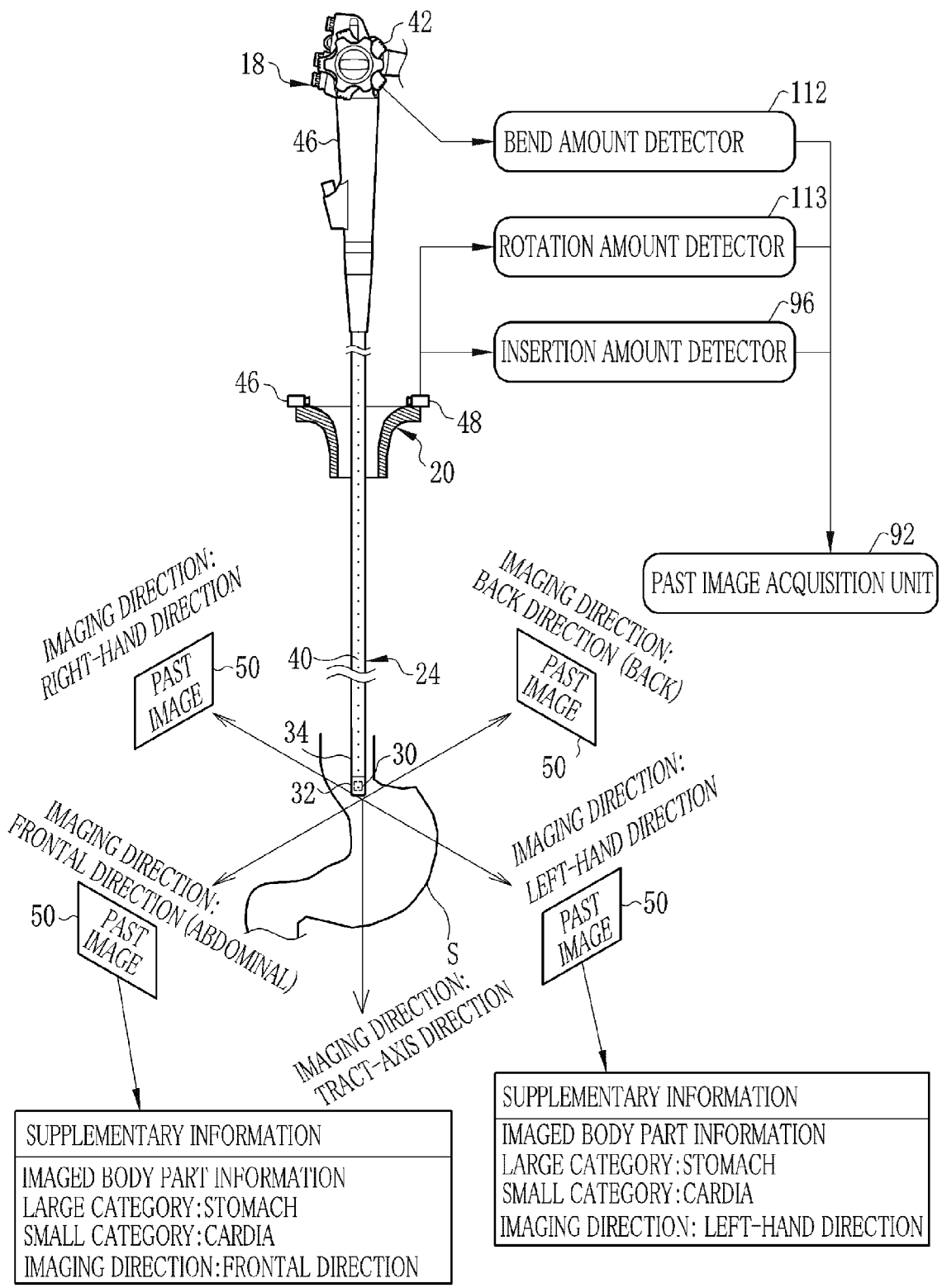
FIG. 11 is an explanatory view illustrating an example in which an insertion amount, a rotation amount, and a bend amount are used to narrow down the past images to be compared with the current image.
Figure 12:
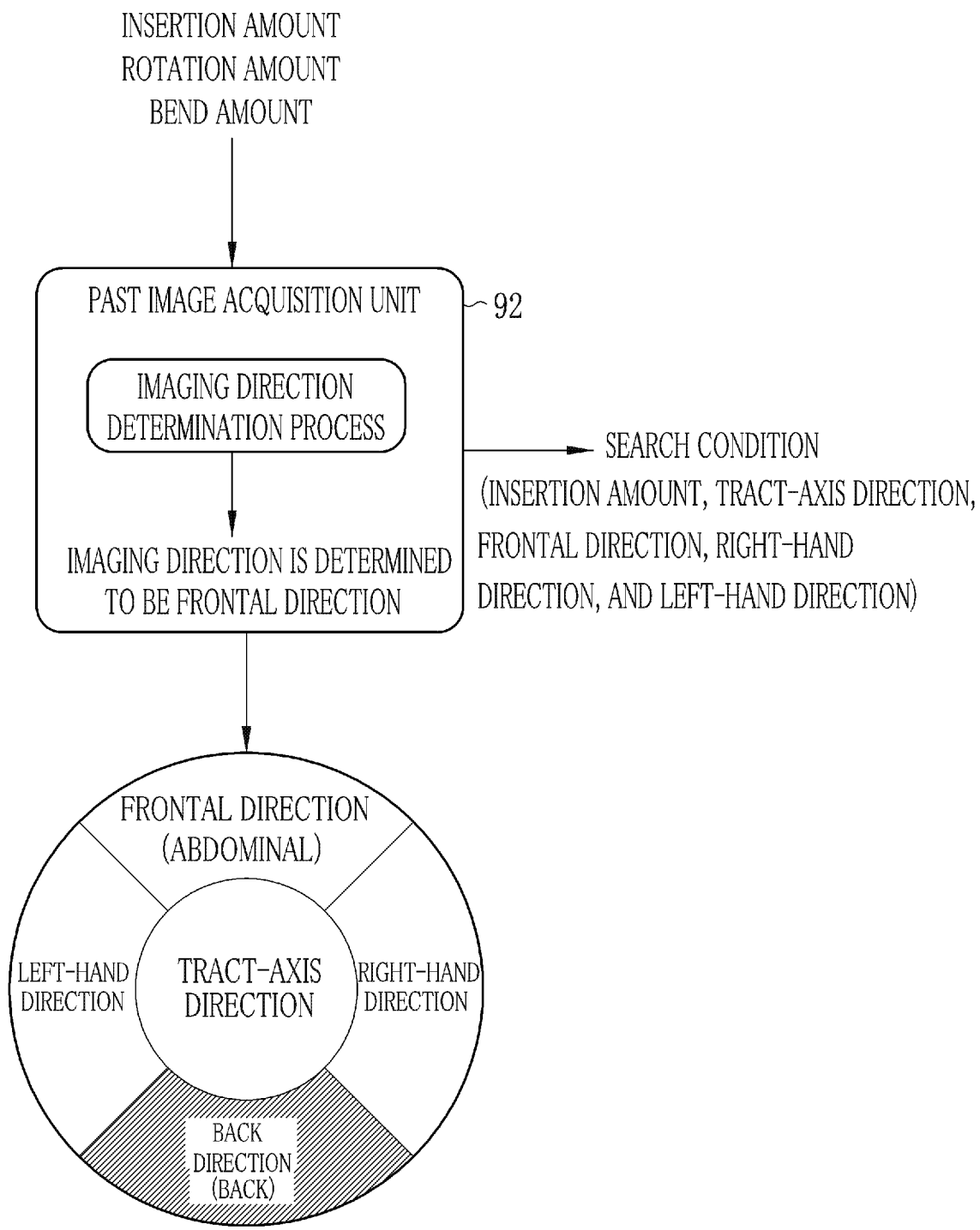
FIG. 12 is an explanatory view illustrating an example in which the insertion amount, the rotation amount, and the bend amount are used to narrow down the past images to be compared with the current image.

In an example of a fourth embodiment illustrated in FIGS. 11 and 12, the past image acquisition unit 92 acquires the past image(s) 50 based on the detected insertion amount, the bend amount of the flexible portion 34, and the rotation amount of the insertion section 24 about the axis. In other words, in the fourth embodiment, the past images 50 to be compared with the current image 49 are narrowed down by the insertion amount, the bend amount, and the rotation amount.

An imaging direction of the distal portion 32 of the endoscope 18 is changed by bending the flexible portion 34. The flexible portion 34 is bent in vertical and horizontal directions by the operation of the angle knob 42. The insertion section 24 is able to rotate about the axis.

In the endoscopic examination, the patient who is the subject of the examination is normally in a side-lying position lying on his side on a table. The insertion direction of the insertion section 24 of the endoscope 18 relative to the patient is often limited or predetermined. For example, in the case where the patient is in the side-lying position with his left side down and his right side up, the insertion section 24 is inserted such that the top of the displayed image corresponds to the patient's right side and the bottom of the displayed image corresponds to the patient's left side. Assuming that the substantially linear upper gastrointestinal tract is located along the body axis of the patient and the relative positional relationship between the position of the patient and the insertion direction of the insertion section 24 is substantially constant, the direction of the distal portion 32 inside the patient's body is detected by detecting the bend amount and the rotation amount. The direction of the distal portion 32 is the imaging direction.

Inside the processor device 22 of this embodiment, the insertion amount detector 91, a bend amount detector 112, and a rotation amount detector 113 are provided. The bend amount detector 112 acquires, for example, the operation mount of the angle knob 42 from the endoscope 18 to detect the bend amount of the flexible portion 34. The angle knob 42 is provided with an angle knob for aiming the flexible portion 34 in the vertical direction and an angle knob for aiming the flexible portion 34 in the horizontal direction. The operation amount (the rotation amount) of the angle knob 42 is detected by a rotary encoder, for example. The detected operation amount is outputted to the bend amount detector 112. Based on the operation amount of the angle knob 42, the bend amount detector 112 detects the bend amount of the flexible portion 34 in the vertical and horizontal directions, and outputs the detected bend amount to the past image acquisition unit 92. The rotation amount detector 113 analyzes the camera images, which are captured by the cameras 46 and 48, to detect the move (shifting) of the scale marks 40 about the axis. Thereby the rotation amount detector 113 detects the rotation amount.

The past image acquisition unit 92 acquires the insertion amount, the bend amount, and the rotation amount in response to the input of the execution start command for the body part identification process. The bend direction relative to a reference position is acquired by detecting the bend amount in the vertical and horizontal directions. The reference position refers to a position in which the bend amount in each of the vertical and horizontal directions is zero and the axis of the distal portion 32 coincides with the axis of the insertion of the insertion section 24. Suppose the direction of the patient and the insertion direction of the insertion section 24 are constant and the upper gastrointestinal tract is located substantially along the body axis, the approximate direction (the imaging direction) of the distal portion 32 is detected based on the bend direction and the rotation amount.

As illustrated in FIGS. 11 and 12, there are five imaging directions, for example. The five imaging directions are a tract-axis direction, in which the axis of a tract such as the gastrointestinal tract coincides with the axis of the insertion of the insertion section 24, and the following four directions described below. The four directions are: a frontal direction (abdominal side or abdominal direction), a back direction (back side), a right-hand direction, and a left-hand direction relative to the patient's body lying on his side with the left side down. Based on the bend amount and the rotation amount, one of the five directions is determined to be the imaging direction of the current image 49. In this example, one of the five imaging directions is recorded as the imaged body part information on each of the past images 50.

As illustrated in FIG. 12, based on the rotation amount and the bend amount, the past image acquisition unit 92 executes an imaging direction determination process for determining the imaging direction. In a case where the imaging direction of the current image 49 is determined to be the frontal direction (the abdominal side), the back direction (the back side) depicted with hatch lines and disposed opposite to the frontal direction (the abdominal side) is eliminated from the five directions. The remaining four directions (the tract-axis direction, the frontal direction (the abdominal side), the right-hand direction, and the left-hand direction) are determined to be the imaging directions that are designated as the search condition.

In this case, only the frontal direction determined by the imaging direction determination process may be designated as the search condition. However, in this example, it is considered that the determination of the imaging direction has a significant error. For this reason, only the imaging direction with the least possibility is eliminated. Thereby the past image(s) 50 of the actual imaging direction are extracted without omission even if the determined imaging direction is different from the actual imaging direction (e.g. in a case where the determined imaging direction is the frontal direction and the actual imaging direction is the right-hand direction).

The purpose of determining the imaging direction is to narrow down the past images 50 that are to be compared with the current image 49. By eliminating only one of or a part of the imaging directions with low possibility, the time for the comparison is reduced. In a case where the determination of the imaging direction has a high degree of accuracy, the direction (the frontal direction in this example)

determined by the imaging direction determination process may be designated as the search condition.

The past image acquisition unit 92 transmits the search request, which contains the determined imaging direction and the insertion amount as the search condition, to the past image server 14 to acquire the past image(s) 50 that matches the search condition.

The body part identifier 98 compares the acquired past image(s) 50 with the current image 49 and determines the past image 50 having high similarity with the current image 49, in a manner similar to the above embodiments. The body part identifier 98 reads the imaged body part and the imaging direction as the imaged body part information, from the supplementary information of the determined past image 50. Thereby the body part identifier 98 identifies the imaged body part in the current image 49 and the imaging direction of the imaged body part. The imaged body part and the imaging direction are displayed as the imaged body part information on the examination support screen 102 in a manner similar to the above embodiments.

In this example, the imaging direction is displayed as the imaged body part information. Thereby the doctor is informed of the imaging direction of the current image 49.

In the above embodiments, the processor device 22 functions as the body part identification device for identifying the imaged body part in the current image 49. Alternatively, a computer such as a server may be provided separately from the processor device 22. The server may function as the body part identification device.

In this case, the information (e.g. the current image 49 captured by the imaging unit 30, the image captured by the camera 46 or 48 provided on the mouthpiece 20, or the operation amount of the angle knob 42) necessary for identifying the imaged body part is transmitted from the processor device 22 to the server. A CPU of the server functions as the current image acquisition unit 90, the past image acquisition unit 92, the insertion amount detector 91, the body part identifier 98, and the like. The past image acquisition unit 92 identifies the imaged body part in a manner similar to the above embodiments, and generates the examination support screen 102, and transmits the examination support screen 102 to the processor device 22. This configuration also achieves effects similar to those described in the above embodiments.

The above embodiments describe the examples in which the cameras 46 and 48 are used to detect the insertion amount and the rotation amount of the insertion section 24. Alternatively, for example, the insertion amount and the rotation amount may be detected by a detection means such as a trackball in a mouse, which is used as an input device for a computer.

Various changes and modifications are possible in the present invention and may be understood to be within the present invention.

What is claimed is:

1. A body part identification device used for an endoscope, the endoscope inserting an insertion section into a body cavity of a patient and capturing an image of the body cavity, a distal portion of the insertion section incorporating an imaging unit, the body part identification device being configured to identify an imaged body part in a current image currently being captured by the imaging unit, the body part identification device comprising:
   a processor configured to perform functions of:
   detecting an insertion amount of the insertion section inserted into the body cavity;
   acquiring the current image;
   acquiring at least one past image from a past image storage unit based on the insertion amount detected by the insertion amount detecting function, the past image storage unit storing the past images captured in at least one past endoscopic examination; and
   identifying the imaged body part in the current image through comparing the past image acquired by the past image acquiring function with the current image and determining the past image similar to the current image,
   wherein the processor is configured to further perform the functions of:
   detecting a bend amount of the insertion section; and
   detecting a rotation amount of the insertion section about an axis of the insertion section, and
   wherein the past image acquiring function acquires the past image based on the insertion amount, the bend amount, and the rotation amount.

2. The body part identification device according to claim 1, wherein identifying the imaged body part comprises determining the past image having the highest similarity with the current image among the past images used for the comparing with the current image, and determining a body part in the determined past image to be the imaged body part in the current image.

3. The body part identification device according to claim 1, further comprising a correspondence table representing correspondence between the insertion amount and a candidate for the imaged body part,
   wherein past image acquiring step comprises referring to the correspondence table and determining the candidate for the imaged body part based on the insertion amount detected by the insertion amount detecting function, and acquiring the past image corresponding to the determined candidate from the past image storage unit.

4. The body part identification device according to claim 1, wherein the past image acquiring function acquires the past image of a patient of interest from the past image storage unit, the patient of interest being imaged in the current image.

5. The body part identification device according to claim 1, wherein the past image acquiring function acquires a past image of another patient from the past image storage unit, the another patient being different from a patient of interest imaged in the current image.

6. The body part identification device according to claim 1, wherein the past image acquiring function acquires a past image of a patient of interest in a case where the past image storage unit contains the past image of the patient of interest and the past image acquiring function acquires a past image of another patient different from the patient of interest in a case where the past image storage unit does not contain the past image of the patient of interest, the patient of interest being imaged in the current image.

7. The body part identification device according to claim 1, wherein the processor is configured to further perform the functions of:
   generating an endoscopic examination support screen, the endoscopic examination support screen displaying the current image and the imaged body part in the current image, the imaged body part being identified by the body part identifying function; and
   controlling a display of the endoscopic examination support screen.

8. The body part identification device according to claim 7, wherein the endoscopic examination support screen displays the current image and the past image in a comparable manner, the past image containing the same imaged body part as in the current image, the imaged body part in the current image being identified by the body part identifying function.

9. A body part identification method used for an endoscope, the endoscope inserting an insertion section into a body cavity of a patient and capturing an image of the body cavity, a distal portion of the insertion section incorporating an imaging unit, the body part identification method identifying an imaged body part in a current image currently being captured by the imaging unit, the body part identification method allowing a body part identification device to perform the steps of:
  detecting an insertion amount of the insertion section inserted into the body cavity;
  acquiring the current image;
  acquiring at least one past image from a past image storage unit based on the insertion amount, the past image storage unit storing the past images captured in at least one past endoscopic examination; and
  identifying the imaged body part in the current image through comparing the acquired past image with the current image and determining the past image similar to the current image,
  detecting a bend amount of the insertion section; and
  detecting a rotation amount of the insertion section about an axis of the insertion section, and
  wherein the past image acquiring function acquires the past image based on the insertion amount, the bend amount, and the rotation amount.

10. A non-transitory computer-readable medium having instructions stored therein, which, when executed by a computer, cause the computer to perform operations for identifying an imaged body part in a current image currently being captured by an imaging unit, the imaging unit being incorporated in a distal portion of an insertion section of an endoscope, the endoscope inserting the insertion section into a body cavity of a patient and capturing an image of the body cavity, the operations comprising:
  detecting an insertion amount of the insertion section inserted into the body cavity;
  acquiring the current image;
  acquiring at least one past image from a past image storage unit based on the insertion amount, the past image storage unit storing the past images captured in at least one past endoscopic examination; and
  identifying the imaged body part in the current image through comparing the acquired past image with the current image and determining the past image similar to the current image,
  detecting a bend amount of the insertion section; and
  detecting a rotation amount of the insertion section about an axis of the insertion section, and
  wherein the past image acquiring function acquires the past image based on the insertion amount, the bend amount, and the rotation amount.

* * * * *